(12) United States Patent
Linares

(10) Patent No.: US 8,257,292 B2
(45) Date of Patent: Sep. 4, 2012

(54) NECK CAST WITH MULTI-POSITION ADJUSTABILITY OF HEIGHT AND DIAMETER AND INCLUDING DOWNWARDLY CONFIGURED SHOULDER SUPPORTS FOR IMMOBILIZING A PATIENT'S HEAD

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 338 days.

(21) Appl. No.: 12/573,299

(22) Filed: Oct. 5, 2009

(65) Prior Publication Data

US 2010/0087764 A1 Apr. 8, 2010

Related U.S. Application Data

(60) Provisional application No. 61/102,500, filed on Oct. 3, 2008.

(51) Int. Cl.
*A61F 5/00* (2006.01)
(52) U.S. Cl. .......................... 602/18; 602/17
(58) Field of Classification Search .............. 602/17–19, 602/5, 32, 36; 128/845, 846, DIG. 23
See application file for complete search history.

(56) References Cited

U.S. PATENT DOCUMENTS

| | | | |
|---|---|---|---|
| 2,807,260 A * | 9/1957 | Teufel | 602/17 |
| 2,820,455 A * | 1/1958 | Hall | 602/18 |
| 3,776,224 A * | 12/1973 | McFarland | 602/18 |
| 4,541,421 A | 9/1985 | Iversen et al. | |
| 4,648,390 A | 3/1987 | Friddle | |
| 5,156,588 A | 10/1992 | Marcune et al. | |
| 5,195,947 A * | 3/1993 | Bode | 602/18 |
| 5,203,765 A | 4/1993 | Friddle, Jr. | |
| 5,575,763 A | 11/1996 | Nagata et al. | |
| 5,697,895 A | 12/1997 | Bremer | |
| 5,964,722 A | 10/1999 | Goralnik et al. | |
| 6,045,522 A | 4/2000 | Grober | |
| 6,210,354 B1 | 4/2001 | Ousdal | |
| 6,368,295 B1 | 4/2002 | Lerman | |
| 6,997,890 B2 | 2/2006 | Stamper et al. | |
| 7,128,724 B2 * | 10/2006 | Marsh | 602/18 |
| 7,371,221 B1 | 5/2008 | Baker | |
| 7,608,052 B1 | 10/2009 | Baker | |
| 2002/0173737 A1 | 11/2002 | Miyaji et al. | |
| 2004/0204666 A1 | 10/2004 | Marsh | |
| 2006/0064005 A1 | 3/2006 | Triano et al. | |

FOREIGN PATENT DOCUMENTS

CN 2772468 Y 4/2006
KR 10-0494071 B1 6/2005

* cited by examiner

*Primary Examiner* — Kim M Lewis
(74) *Attorney, Agent, or Firm* — Gifford, Krass, Sprinkle, Anderson & Citkowski, P.C.

(57) ABSTRACT

The present invention teaches a head and neck cast for providing secure immobilization of a patient's upper neck and head extremities and includes a lower ergonomically configured ring supported upon the shoulders of the wearer. An upper ring is vertically displaceable in each of upper and lower directions relative to the lower support ring via an interconnecting network of both scissoring and vertically extending jacks. In this fashion, the neck and head of the patient is immobilized via the positional support provided by the lower ring and without the need for screws mounted to the skull.

19 Claims, 6 Drawing Sheets

NECK CAST WITH MULTI-POSITION ADJUSTABILITY OF HEIGHT AND DIAMETER AND INCLUDING DOWNWARDLY CONFIGURED SHOULDER SUPPORTS FOR IMMOBILIZING A PATIENT'S HEAD

CROSS REFERENCE TO RELATED APPLICATIONS

The present application claims the benefit of U.S. Provisional Patent Application Ser. No. 61/102,500, filed Oct. 3, 2008.

FIELD OF THE INVENTION

The present invention relates generally to head and neck immobilizing articles. More specifically, the present invention discloses a head and neck cast exhibiting varying configurations for adjusting either or both a height or width dimension associated with the cast and for providing proper and immobilizing support to the head and neck of the wearer, relative to the wearer's shoulders, without the need of mounting screws implanted into the user's skull and in use with an associated halo.

DESCRIPTION OF THE PRIOR ART

The prior art is documented with examples of head and neck immobilizing structure, such as for use in preventing movement of the head and neck in course of treating spinal cord injuries and the like. One known device incorporates the use of a patient or stationary mounted halo surrounding the head and which is utilized in combination with a plurality of screws implanted into the wearer's skull. The screws are attached, via such as a strong and thin nylon or like synthetic filament, to locations of the encircling halo.

SUMMARY OF THE PRESENT INVENTION

The present invention teaches a head and neck cast for providing secure immobilization of a patient's upper neck and head extremities and includes a lower ergonomically configured ring supported upon the shoulders of the wearer. An upper ring is vertically displaceable in each of upper and lower directions relative to the lower support ring via an interconnecting network of both scissoring and vertically extending jacks. In this fashion, the neck and head of the patient is immobilized via the positional support provided by the lower ring and without the need for screws mounted to the skull.

Additional features include the provision of first and second pairs of scissor jacks extending between the lower and upper rings. A diameter of at least one of the upper and lower rings may further be adjustable through actuation of the scissor jacks. Other features include cushioning layers associated with each of the upper and lower rings. Additional features include such as a pair of side positioned and adjustable head stabilizer portions which can be secured atop the upper ring, such further being adjustable in either of first and second axial directions.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Referring now to the illustrations of FIGS. 1-6, the present invention discloses a head and neck cast exhibiting varying configurations for adjusting either or both a height or width dimension, such as for providing proper and immobilizing support to the head and neck of the wearer. As will also be discussed, the head and neck cast additionally provides laterally adjustable head stabilizers for immobilizing the wearer's head, and without the need of mounting screws implanted into the user's skull and such as which are typically employed with conventional halo designed head and neck casts.

Figure 1:
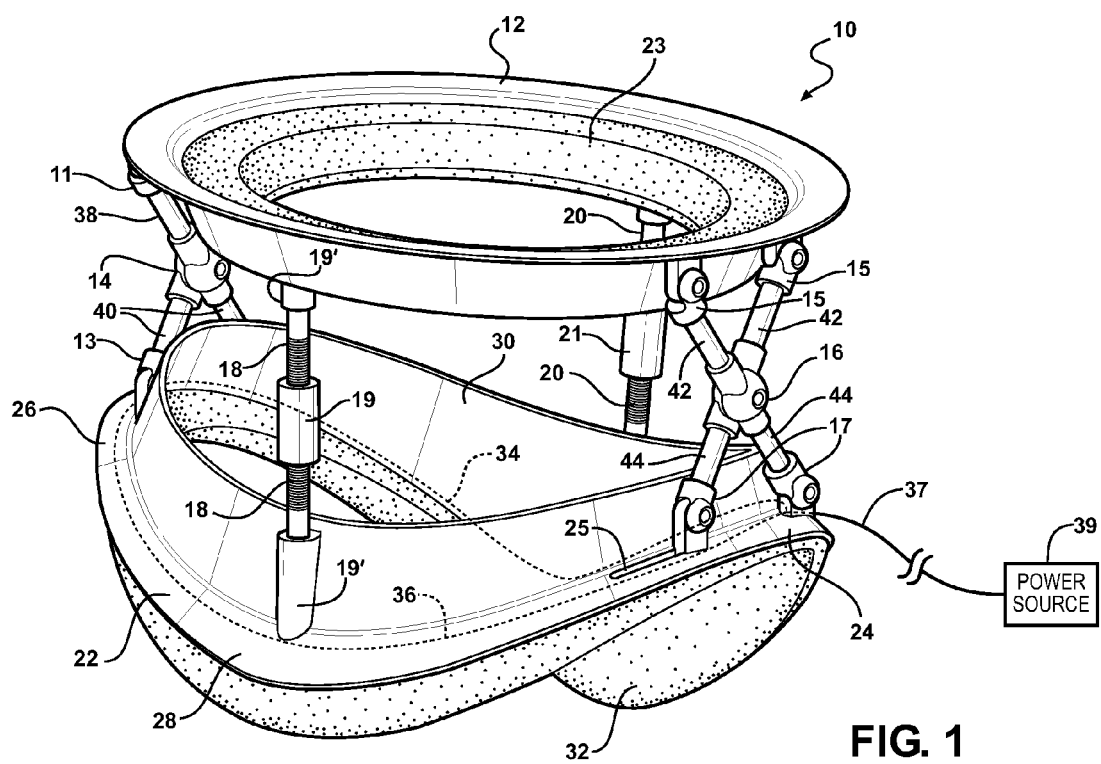
FIG. 1 is an illustration of a neck cast according to a first embodiment and showing the features of the vertical adjustability of the upper head cushioning and supporting ring, via the pairs of elevating/lowering scissor jacks supporting the upper ring upon the lower shoulder/back supporting ring.
Figure 2:
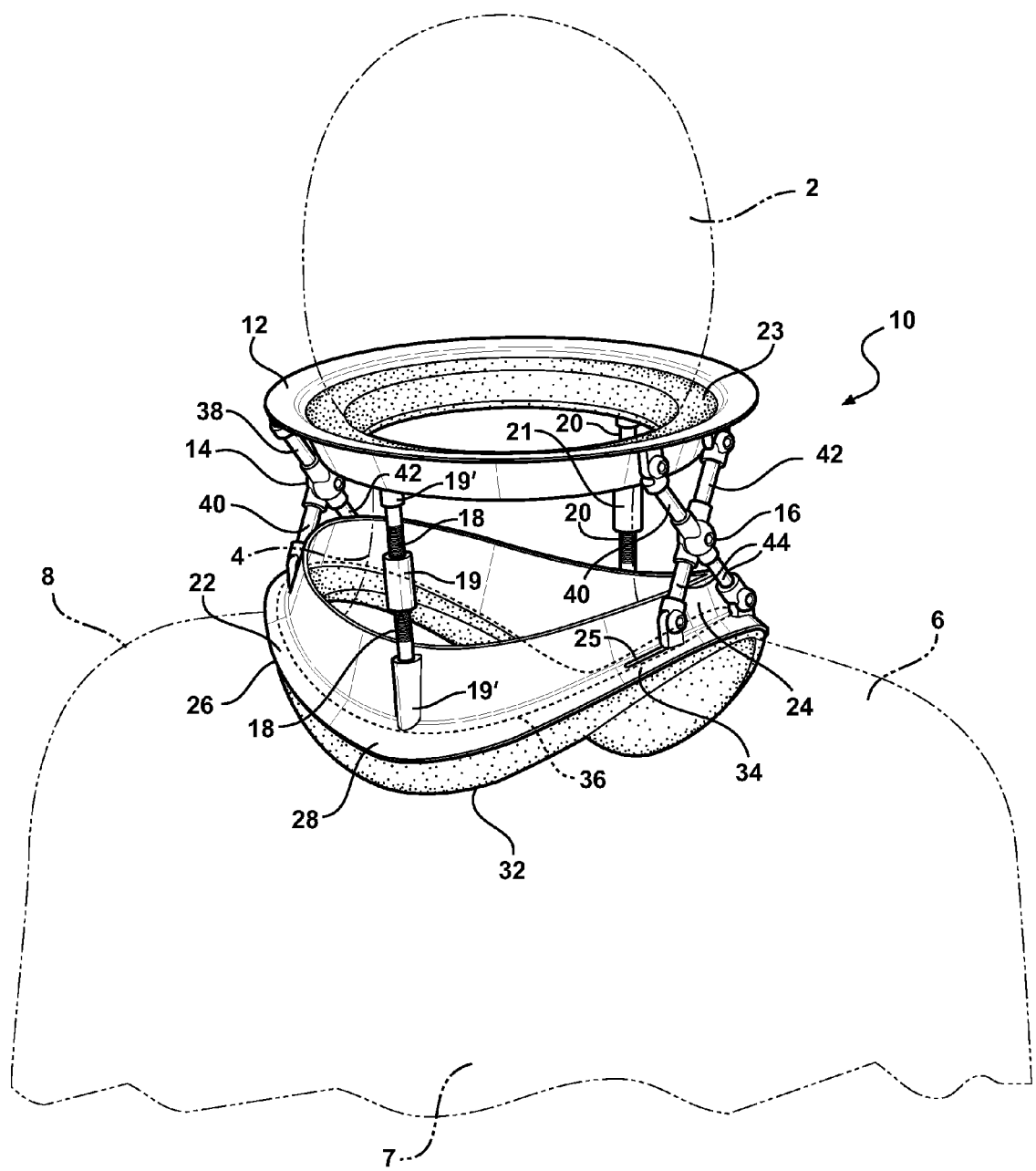
FIG. 2 is an environmental view of the head and neck cast of FIG. 1 as worn by a user and illustrating the manner in which the upper/elevated ring portion immobilizes the user's head.
Figure 3:
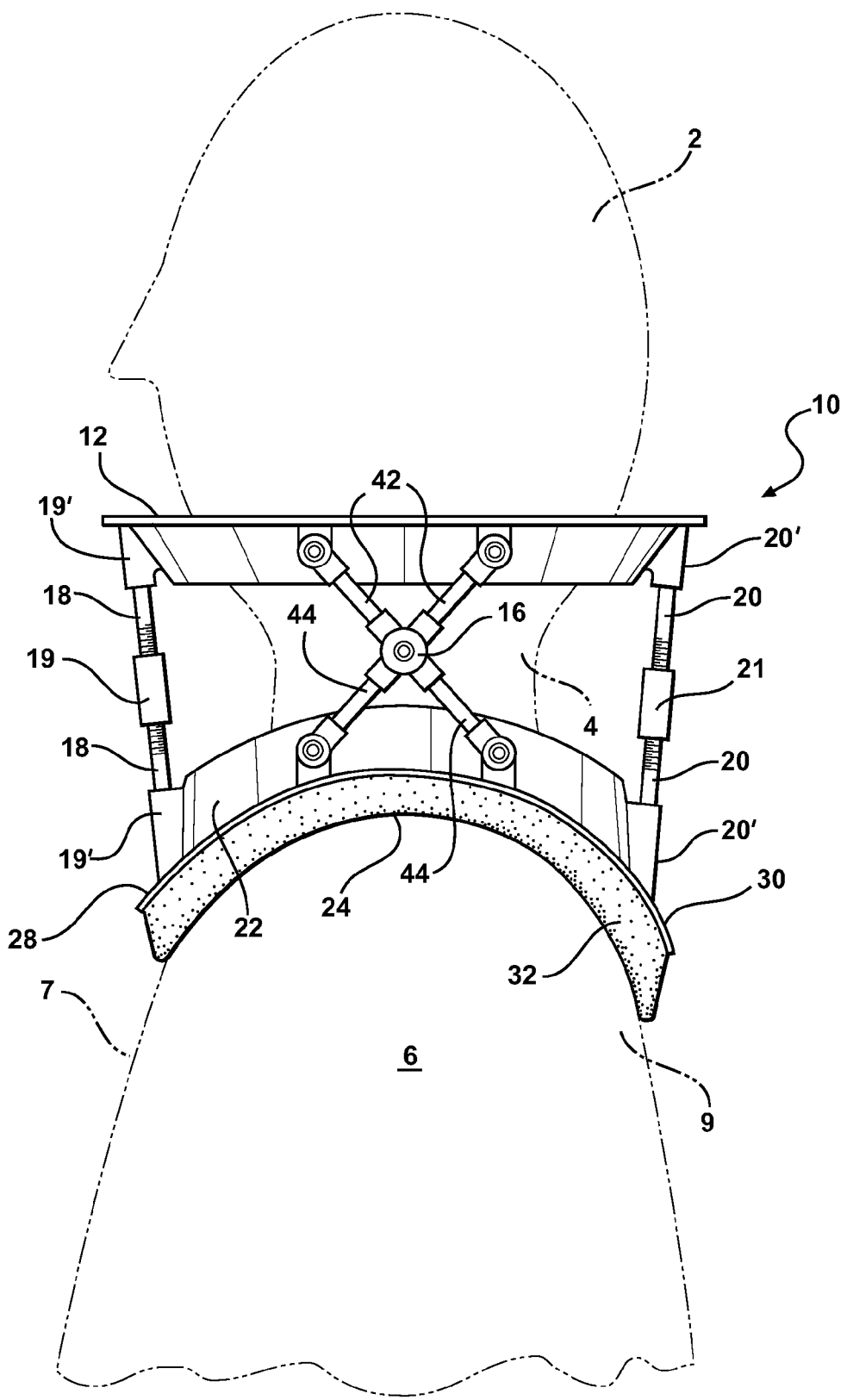
FIG. 3 is a rotated side view of the environmental illustration of FIG. 2.

Referring first to FIGS. 1-3, an illustration is shown at 10 of a neck cast according to a first embodiment. The neck cast 10, as will be described, is typically constructed of a durable and impact resistant plastic or other suitable material and employs the features of vertical adjustability of an upper cushioning, encircling and structural supporting member, hereinafter referred to as an upper ring 12. This is provided via individual scissor jacks, see as shown at each of 14 and 16 in reference to each of first and second intermediate and pseudo-X shaped housings.

In any of a number of non-limiting construction, the legs or pillars associated with the scissor support housings 14 and 16 (such as are further referenced at 38-44) can be configured in elongated and angularly disposed fashion relative to one another and in order to permit the overall length of the end to end aligning pillars to be modified in either a lengthened or shortened fashion and so that the upper ring 12 is vertically displaceable in up and down directions, this in concert with alternating elevating/lowering (aligning) jacks which are each identified by pairs 18 and 20 of end to end extending threaded rods, these collectively supporting the upper ring 12 at varying elevations relative to a lower encircling, shoulder/back and ergonomically configured structural supporting member, hereinafter referred to as a lower ring 22. It is also envisioned that such modifications to the scissor support housings 14 and 16 and associated legs 38-44 can include length adjustability via a ratchet and teeth arrangement and which also includes adjustability inducing features built into the support housings 14 and 16 (such as a catch or trigger for permitting the individual pillars to be readjusted).

As further shown, pairs of upper and lower pivotal end connections can be incorporated into each of the scissor jack assemblies and which are shown at 11 and 13 in reference to scissor jack 14 and further at 15 and 17 in reference to scissor jack 16. Concurrently, the single offset positioned jacks may also incorporate such as intermediate positioned and internally threaded turn buckle portions 19 and 21 for engaging extending locations of the exteriorly threaded and end-to-end arranged pairs 18 and 20 of linearly opposing threaded rods, the rods in turn seating within configured receptacles, e.g. at 19' for each end of rods 18 and further at 20' for each end of rods 20 associated with each of the upper ring 12 and lower structural supporting portion 22. The construction of the scissor jacks, as shown, is such that either or both the lower interconnecting end of each scissor jack leg or pillar support can linearly displace along a slot or channel (see extending slot 25 which linearly displaceably supports lower selected pivotal connection 17 associated with scissor jack 16) to provide combined height and width adjustment of the respective legs/pillars 42 and 44.

It is also envisioned that the end connections can be non-pivoting (e.g. rigid or fixed) in combination with incorporating a variant of scissor jacks in which all requisite multi-dimensional displacement occurs at the intermediate housings 14 and 16 (e.g. accommodation to both the horizontal and vertical components occurs at the housings 14 and 16 and by which the individual pairs of legs 38-44 each extend or retract in a direction from the intermediate housings so as not to create any pivoting or rotating forces upon the end connections shown at 11, 13, 15 and 17. Alternatively, it is also envisioned that the arrangement illustrated can be substituted for another scissor like pattern incorporating telescoping pillar supports or other structure for providing controlled raising and lowering of the upper ring 12 relative to the lower ring 22.

As further illustrated in the operational views of FIGS. 2 and 3, the cast 10 is configured so that the upper support ring 12 exhibits a substantially annular/ring shape which, when installed, surrounds and supports the underside perimeter of the user's jaw and skull (this while still permitting a degree of mandibular movement) and encircles the boundary location generally existing between the wearer's head 2 and neck 4. An inner rim of the upper support ring 12 exhibits a layer of foam or other suitable cushioning material (at 23 in FIGS. 1 and 2) and provides the desired degree of positioning and support of the wearer's head.

The lower shoulder/back supporting portion 22 (also ring shaped) exhibits a generally undulating and arcuate/ergonomic promoting underside perimeter configuration, this in order that it is supported evenly and ergonomically around the wearer's collar bone (not shown), and further so that upwardly curved side locations 24 and 26 of the lower ring portion 22 are positioned proximate the wearer's shoulders 6 and 8. As further shown in each of FIGS. 2 and 3, front 28 and rear 30 locations of the lower ring 22 (these alternating with the upwardly curved side locations 24 and 26) substantially overlay the front (upper breastbone) 7 and rear (back) 9 locations of the wearer's upper torso. A further layer of any type of foam or like cushioning material, see as shown at 32, is provided in encircling fashion around an underside and downwardly facing rim or surface of the lower support ring 22 for establishing cushioning support when being worn.

The side positioned pairs of scissor jacks establish, in a preferred embodiment, powered driving or operating jacks and which are powered by such as servo actuating motors (not shown) which can be incorporated into locations in contact with the extending legs or pillars (see for example intermediate support housings 14 and 16). Wires (or other operational guide lines) are referenced at 34 and 36 in FIG. 1 in extending fashion between the individual pairs of scissor jacks 14 and 16. A further line 37 extends from such as a conjoined location of the guide lines 34 and 36, to another suitable location at which an electrical power or activating input source 39 is provided via the wires 34 and 36, such as which can further extend internally along locations approximate each scissor jack assembly and in order to activate/actuate the scissor jacks in simultaneous manner.

In this fashion, the side positioned pairs of scissor jacks 14 and 16 are operated in tandem in order to elevate or lower the upper support ring 12 relative to the lower arcuate base support ring 22. The offset and linear turnbuckle supported pairs of threaded rods 18 (for turnbuckle 19) and 20 (for turnbuckle 21) are further in a preferred embodiment are not powered, but rather provide controlled and stabilizing support to the alternating locations of the upper support ring 12, concurrent with the powered/mechanical vertical displacement initiated at either pair of scissor jack locations 14 and 16. In order to prevent misalignment or eccentric between the scissor jacks 14 and 16 and the offset turnbuckle supports, it is also envisioned that controlled and/or simultaneous elevating of both sets of jacks can be employed or further that such as the turnbuckle supports 19 and 21 can be temporarily removed/disabled during selective and concerted elevation of the scissor jacks 14 and 16, following which the turnbuckles are reattached and adjusted to a supporting length achieved by the repositioned scissor jacks.

Although not specifically shown, it is envisioned and understood that the scissor jacks 14 and 16 may contain any appropriate structure (be it electrically/servo, mechanically, hydraulic or pneumatically actuated) including such as integrally incorporated and powered controls for selectively extending/retracting either of its upper and/or lower extending legs (see again at 38 and 40 for jack 14 and further at 42 and 44 for jack 16. As previously described, the individual sets of legs 38-44 seat within either fixed or (as shown) pivotally associated locations associated with the upper 12 and lower 22 support rings, as well as engaging opposite locations of the intermediate X-shaped housings (generally identified at 14 and 16), these selected locations again defining any of telescoping or linear (end to end) displaceable engagement locations. Additional to previous alternate structure, another preferred application contemplates one or more of the displaceable legs 38-44 employing a mechanical screw or the like (with the remaining legs being fixed at either or both ends) and which is telescopically threaded so that, upon rotation, the individual pairs of scissor jack supporting legs are actuated and thereby cause the upper support ring 12 to elevate or lower relative to the lower and back/shoulder supported ring.

In this fashion, a correct vertical height/position of the upper ring 12 can be established, upon pre-positioning of the cast 10 upon the wearer's shoulder, and at which point the foam interior 24 of the upper ring provides an appropriate degree of cushioning support. Concurrently the lower support ring 22 provides a likewise degree of desired support upon the user's shoulders, front and back and, by virtue of being prevented from moving by the numerous contact locations established with the wearers upper body, this immobilizing support is transferred to the upper ring 12 via the various lifting jacks 14, 16, 18 and 20 positioned about its interconnecting perimeter. The upper support ring 12 can further be configured with overlapping edges (not shown) this in order to adjust its diameter to coincide with the angled/height adjustment jacks and so that, upon elevating the individual legs of the crosswise extending jacks, the overall diameter of the upper support ring 12 is decreased whereas, and upon lowering the individual legs, the overall diameter is increased.

Figure 4:
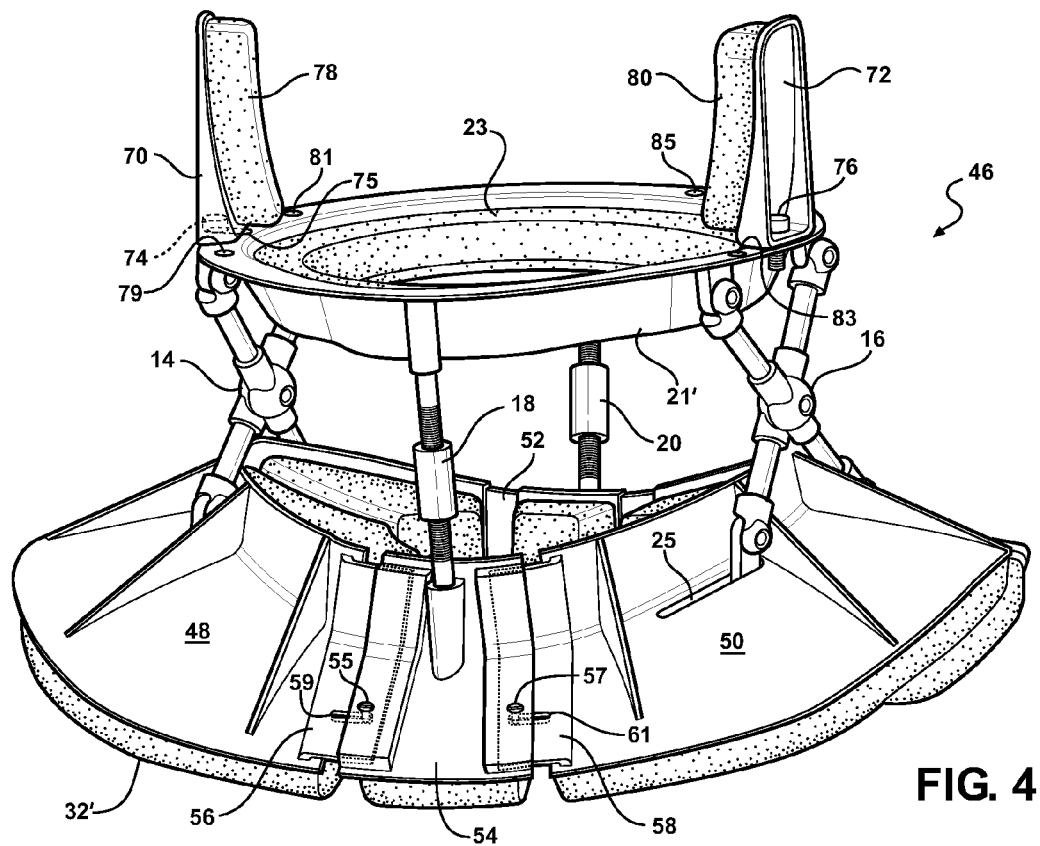
FIG. 4 is an illustration of a pseudo-halo version of a head and neck cast according to a further preferred embodiment and illustrating the features of width adjustability of the lower shoulder/back supporting portion, in combination with a pair of side mounted and opposing/laterally adjustable head stabilizers positioned in upwardly extending fashion upon the upper cushioning and supporting ring and for contacting opposite sides of the wearer's head for providing immobilizing support.
Figure 5:
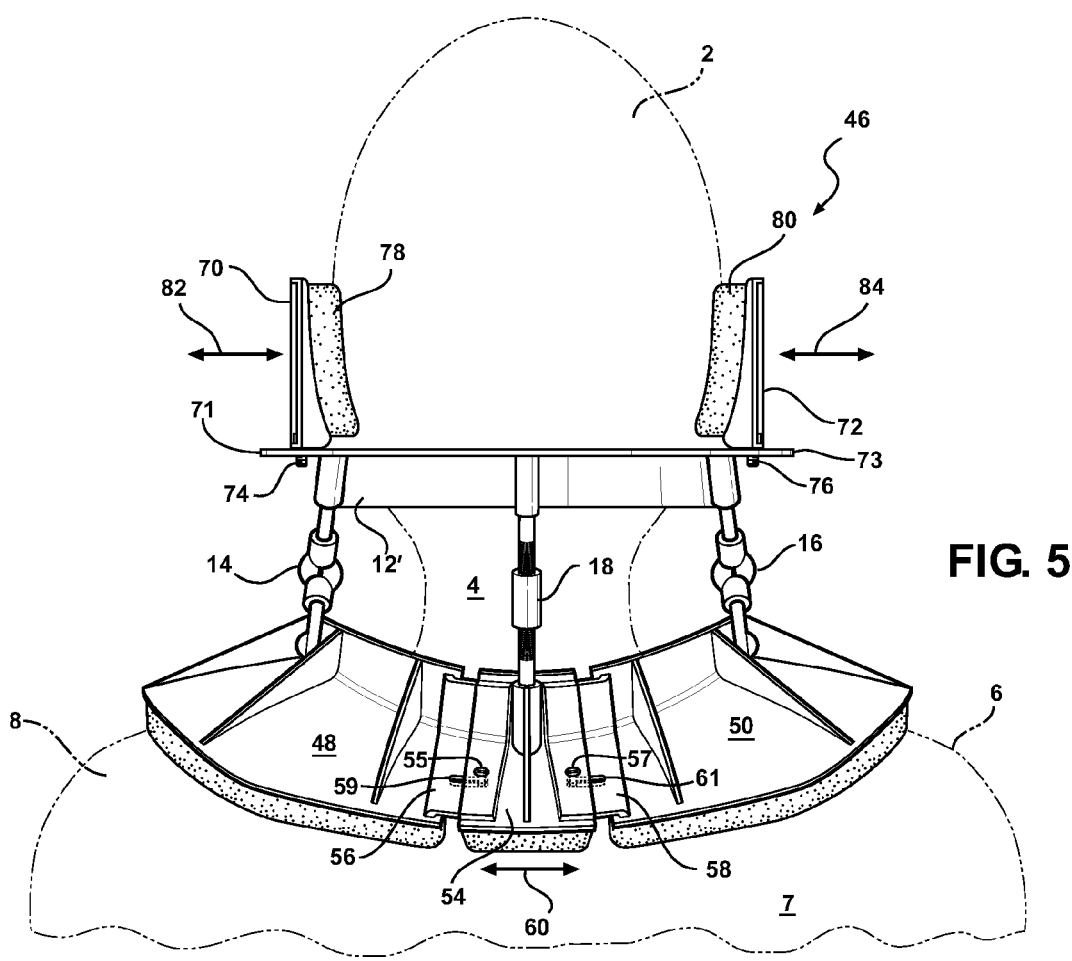
FIG. 5 is an operational front view of a halo version of a head and neck cast as shown in FIG. 4.
Figure 6:
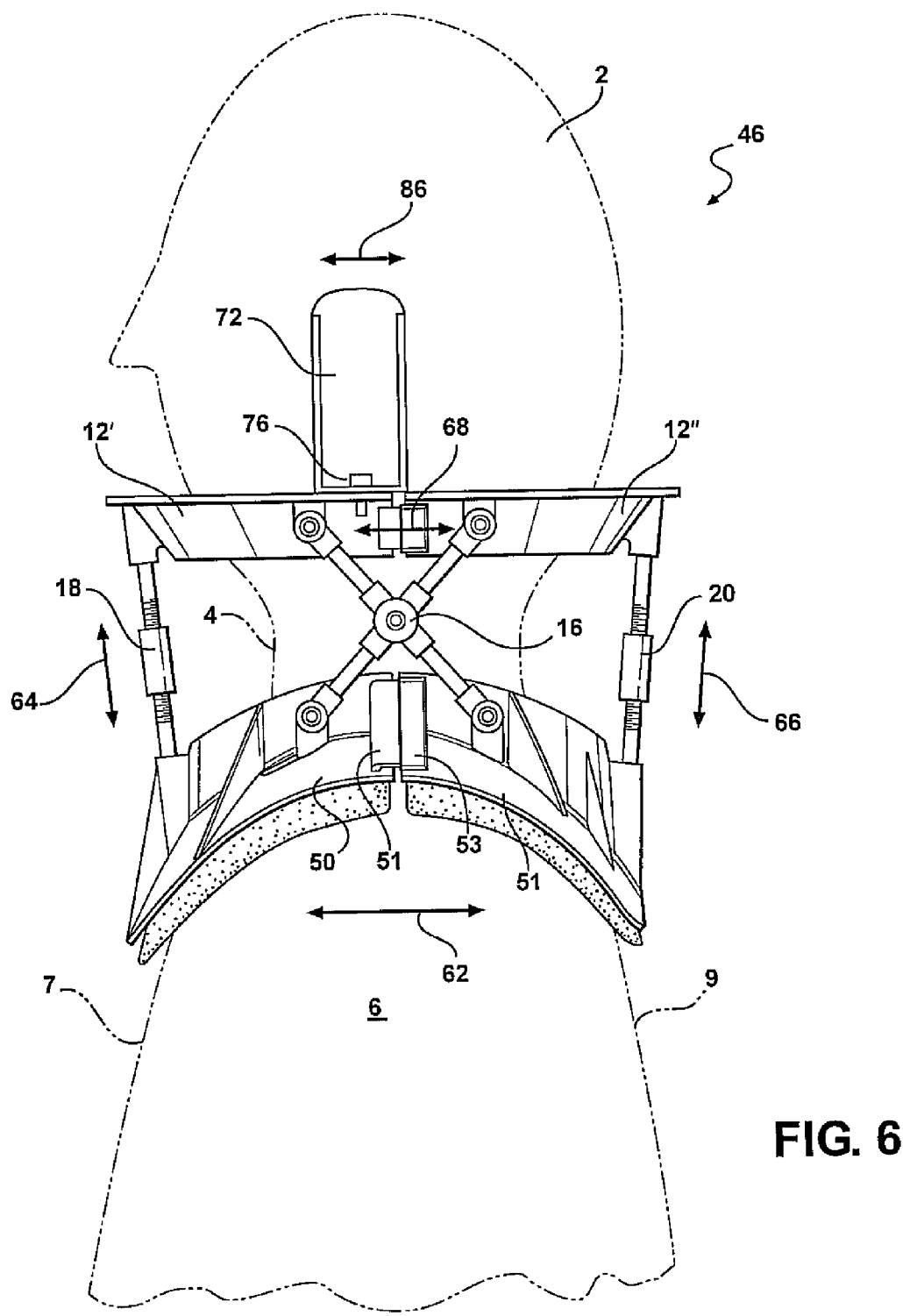
FIG. 6 is a rotated side view of the head and neck cast of FIG. 4.

Referring now to FIGS. 4-6, a halo/immobilizing version of a head and neck cast is illustrated at 46 according to a further preferred embodiment. The version 46 is similar in numerous respects to that previously disclosed at 10, such that identical features including the scissor jacks 14 and 16 and turnbuckle actuated jacks 18 and 20 are not repetitively described in detail. As will be described in detail, the variant 46 illustrated includes the addition of specified width adjustability of the lower shoulder/back support ring, as well as the provision of a pair of opposing and laterally adjustable head stabilizers, these positioned upon the upper cushioning and supporting ring, and for immobilizing the wearer's head 2 without the need for screws or the like often associated with prior art halo-type designs.

The above said, elements of the halo version 46 identical to that of the head/neck cast 10 are identically numbered and again include the features of the upper support ring (shown as split ring portions 12' and 12"), and in addition to side pairs 14 and 16 of scissor jacks and alternating front 18 and rear 20 support jacks, as well as cushioning foam support 23 associated with upper split rings 12' and 12" and a likewise reconfigured lower surface rim/perimeter extending cushioning layer 32', this further being broken into segments associated with each of succeeding and overlapping perimeter defining portions 48, 50, 52. The lower support ring is modified from the fixed/one piece design previously illustrated at 22 in the embodiment 10 and, as shown in FIGS. 4-6, includes main portions 48 and 50 with alternating rear 52 and front 54 portions.

As further shown, overlapping locations are established between the individual and perimeter defining lower (split) ring defining portions 48, 50, 52 and 54, these being best shown at 56 and 58 in FIGS. 4 and 5 and in relation to opposite edges of forward most positioned split ring portion 54. Additional side adjustability is illustrated by overlapping portions 51 and 53 in FIG. 6, and as further referenced by selectively illustrated subset split portion 51 positioned between split portions 50 and 52 and, via overlapping edge 57 which aligns with opposing edge 55 associated with split portion 50, permits a further degree of side adjustability. A further rear split portion is also contemplated in position between the ring portions 48 and 52 but is not shown.

In use, this arrangement allows for a desired range of harness adjustment (see arrows at 60 and 62 in FIGS. 5 and 6 respectively) in order that the lower support portions 48, 50, 51, 52 and 54 are properly sized in circumference according to some range of adjustability and in order to seat upon the wearer's upper body and shoulders. The overlapping locations defined around the various and main perimeter assembling pieces 48, 50, 52 and 54 are further capable of being circumference adjusted by manual input or, alternatively, as an incident to actuation of the (powered) scissor jacks. Positional locking fasteners, see as exemplary shown at 55 and 57 incorporated into overlapping edge 56 and 58 in FIGS. 4 and 5, can also be provided and which seat at defined locations along slots or recess channels 59 and 61 associated with the underside overlapping surfaces of adjoining split ring portions 48 and 50.

As further previously described in reference to the first embodiment 10, the scissor jacks 14 and 16 operate in substantially the same fashion to selectively elevate or lower the upper ring portion 12 (see vertical adjustment arrows 64 and 66 in FIG. 6) into a desired and cushioning support of the user's head 2 and neck 4, it being further understood that the operation of the scissor jacks can cause the desired width/harness telescoping adjustment of the lower ring support portions 48-54, this further given the contacting locations of the various scissor jack legs relative to additional (and upper end) contact locations which engage fixed points around the underside periphery of the upper fixed support ring. As further shown in FIG. 6, the upper support ring can alternatively exhibit a chin width adjustment feature, see arrow 68, and by which linearly overlapping portions associated with each of the front and rear subset ring portions 12' and 12" collectively defining the upper ring can be diameter adjustable to properly support the ring underneath the user's jaw.

Head stabilizers are shown at 70 and 72, each consisting of an upwardly extending bridge or superstructure portion which is pin supported, see respectively at 74 and 76, to an upper side surface location of the upper support ring 12. Each of the head stabilizers further includes an inner positioned and foam cushioning insert, see at 78 and 80 in FIGS. 4 and 5, and which contact side locations of the wearer's head 2.

The head stabilizers 70 and 72 are constructed so that they are capable of being displaced in either or both of laterally (in/out) axial directions, see at 82 and 84 in FIG. 5, and/or in forward/rearward axial directions (see at 86 in FIG. 6) relative to the upper support ring 12. This desired degree of adjustability is provided by the ability to move the stabilizers 70 and 72 in and out (along the direction of arrows 82 and 84 in FIG. 4) and by providing a degree of width adjustment between the pins 74 and 76 and annular surface of the upper split ring portions. This can include either or both of widening the annular surfaces at aligning locations (see at 71 and 73 in FIG. 5) or, alternatively, of integrating width adjustable slots (see further at 75 in FIG. 4 for selected head stabilizer 70).

The upper support ring is further configured with either of linearly extending side channels (not shown) and/or multiple seating locations (see as shown by spaced apart apertures 79 and 81 for stabiliser 70 as well as corresponding spaced apertures 83 and 85 for stabilizer 72), and in order to provide additional perimeter readjustment (see arrow 86 in FIG. 6). The slots or apertures are defined through the annular ring surface of the upper split ring portions 12' and 12" for receiving the engagement pins (these also contemplated to include selectively tightened screws) 74 and 76 associated with the head stabilizers 70 and 72, and for selectively repositioning the head stabilizers in a fixed manner. In this manner, the adjustable halo variant 46 of FIGS. 4-6 provides all of the features of the fixed perimeter head/neck support variant 10, without the requirement for inserting skull screws or the like, and which is common with certain neck fractures.

Having described my invention, other and additional preferred embodiments will become apparent to those skilled in the art to which it pertains, and without deviating from the scope of the appended claims:

I claim:

1. An immobilizing head and neck device, comprising:
   a structural supporting member with an ergonomically configured lower surface for supporting upon at least the shoulders of a wearer;
   an upper ring supported in vertically displaced manner relative to the structural supporting member, said upper ring providing positional support to the user's jaw and head;
   a plurality of jacks arranged in spaced apart and opposite end contacting fashion around a perimeter associated with each of said supporting member and upper ring; and said upper ring further comprising first and second assemble-able and split ring portions, said structural supporting member further comprising a plurality of end-to-end overlapping and perimeter defining portions.

2. The invention as described in claim 1, further comprising first and second scissor jacks arranged at side locations associated with said supporting member and upper ring.

3. The invention as described in claim 2, further comprising linearly extending and turnbuckle actuated jacks arranged at front and rear locations associated with said supporting member and upper ring and offset from said scissor jacks.

4. The invention as described in claim 3, each of said turnbuckle adjustable jacks further comprising a pair of end to end extending and exteriorly threaded rods.

5. The invention as described in claim 2, each of said scissor jacks further comprising a plurality of elongated and angularly disposed legs extending from an intermediate support housing for engaging said supporting member and said upper ring and according to at least one of a fixed, pivotal, or displaceable fashion.

6. The invention as described in claim 5, further comprising a pair of lengthwise slots formed in a surface of said structural supporting member and facilitating linear displacement of at least one leg associated with each scissor jack.

7. The invention as described in claim 2, further comprising a servo actuating motor associated with said scissor jacks and powered by at least one wire extending between said scissor jacks.

8. The invention as described in claim 5, further comprising said head stabilizers being adjustable in at least one of width or perimeter adjustable fashion.

9. The invention as described in claim 1, further comprising a diameter of at least one of said upper ring and structural supporting member being adjustable through actuation of said scissor jacks.

10. The invention as described in claim 1, further comprising aligning slots and fasteners associated with at least one overlapping location established between successive perimeter defining portions.

11. The invention as described in claim 1, further comprising a cushioning layer associated with each of an inner surface associated with said upper ring and a lower surface associated with said structural supporting member.

12. The invention as described in claim 1, further comprising a pair of side positioned and adjustable head stabilizer portions secured atop said upper ring.

13. An immobilizing head and neck device, comprising:
a structural supporting member with an ergonomically configured lower surface for supporting upon at least the shoulders of a wearer;
an upper ring supported in vertically displaced manner relative to the structural supporting member, said upper ring providing positional support to the user's jaw and head;
said upper ring further comprising first and second assemble-able and split ring portions, said structural supporting member further comprising a plurality of end-to-end overlapping and perimeter defining portions; and
a plurality of jacks arranged in spaced apart and opposite end contacting fashion around a perimeter associated with each of said supporting member and upper ring and including first and second scissor jacks arranged at side locations associated with said supporting member and upper ring, a pair of linearly extending and turnbuckle actuated jacks arranged at front and rear locations associated with said supporting member and upper ring and offset from said scissor jacks.

14. The invention as described in claim 13, each of said scissor jacks further comprising a plurality of elongated and angularly disposed legs extending from an intermediate support housing for engaging said supporting member and said upper ring and according to at least one of a fixed, pivotal, or displaceable fashion.

15. The invention as described in claim 13, further comprising a pair of lengthwise slots formed in a surface of said structural supporting member and facilitating linear displacement of at least one leg associated with each scissor jack.

16. The invention as described in claim 13, further comprising a diameter of at least one of said upper ring and structural supporting member being adjustable through actuation of said scissor jacks.

17. The invention as described in claim 13, further comprising aligning slots and fasteners associated with at least one overlapping location established between successive perimeter defining portions.

18. An immobilizing head and neck device, comprising:
a structural supporting member with an ergonomically configured lower surface for supporting upon at least the shoulders of a wearer;
an upper ring supported in vertically displaced manner relative to the structural supporting member, said upper ring providing positional support to the user's jaw and head; and
a plurality of jacks arranged in spaced apart and opposite end contacting fashion around a perimeter associated with each of said supporting member and upper ring, said jacks including first and second pairs of scissor jacks hingedly connected at opposite outer ends to locations along said structurally supporting member and said upper ring as well as pivotally interconnected at midpoint locations and to establish a desired separation distance between said supporting member and upper ring, in combination with adjusting a perimeter dimension associated with at least one of said supporting member and upper ring.

19. The invention as described in claim 18, said jacks further comprising pairs of end-to-end extending threaded rods arranged at perimeter offset locations relative to said scissor jacks and which extend from said supporting member and said upper ring, a rotatable turnbuckle receiving opposing inserting ends of each of said pair of rods and which are adjustable along with said scissor jacks.

* * * * *